United States Patent
Rey et al.

(10) Patent No.: US 7,745,624 B2
(45) Date of Patent: Jun. 29, 2010

(54) PREPARATION OF ACID ADDITION SALTS OF ZIPRASIDONE AND INTERMEDIATES THEREOF BY SOLID PHASE-GAS PHASE REACTIONS

(75) Inventors: Allan W. Rey, Brantford (CA); Lotfi Derdour, Brantford (CA); K.S. Keshava Murthy, Ancaster (CA); Probal Kanti Datta, Brantford (CA); Martin Ehlert, Branchton (CA); Stephen E. Horne, Burlington (CA)

(73) Assignee: Apotex Pharma Chem Inc., Brantford (CA)

( * ) Notice: Subject to any disclaimer, the term of this patent is extended or adjusted under 35 U.S.C. 154(b) by 1312 days.

(21) Appl. No.: 11/168,524

(22) Filed: Jun. 29, 2005

(65) Prior Publication Data
US 2006/0205947 A1    Sep. 14, 2006

(30) Foreign Application Priority Data
Mar. 11, 2005    (CA) .................................... 2500667

(51) Int. Cl.
*C07D 241/00*    (2006.01)
*C07D 241/02*    (2006.01)

(52) U.S. Cl. ...................................................... 544/336

(58) Field of Classification Search ................ 514/247, 514/254; 544/336
See application file for complete search history.

(56) References Cited

U.S. PATENT DOCUMENTS

| | | | |
|---|---|---|---|
| 4,831,031 A * | 5/1989 | Lowe et al. ............ 514/254.02 |
| 5,312,925 A | 5/1994 | Allen et al. | |
| 5,935,960 A | 8/1999 | Walinsky et al. | |
| 6,150,366 A | 11/2000 | Arenson et al. | |
| 2005/0043324 A1 | 2/2005 | Koltai et al. | |
| 2005/0049295 A1 | 3/2005 | Reddy et al. | |

FOREIGN PATENT DOCUMENTS

| | | | |
|---|---|---|---|
| CA | 2252898 | | 11/1997 |
| CA | 2467538 | * | 5/2004 |
| WO | WO-2004/050655 A1 | | 6/2004 |
| WO | WO-2004/054621 A1 | | 7/2004 |
| WO | WO-2004/089948 A1 | | 10/2004 |

* cited by examiner

*Primary Examiner*—James O. Wilson
*Assistant Examiner*—Paul V. Ward
(74) *Attorney, Agent, or Firm*—Apotex, Inc.

(57) ABSTRACT

A process for the preparation of an acid addition salt of ziprasidone base and intermediates thereof comprising exposing the ziprasidone base in solid form to a gaseous acid in a substantially dry environment.

79 Claims, 1 Drawing Sheet

Figure 1. PXRD Diffractogram of Amorphous Ziprasidone Hydrochloride
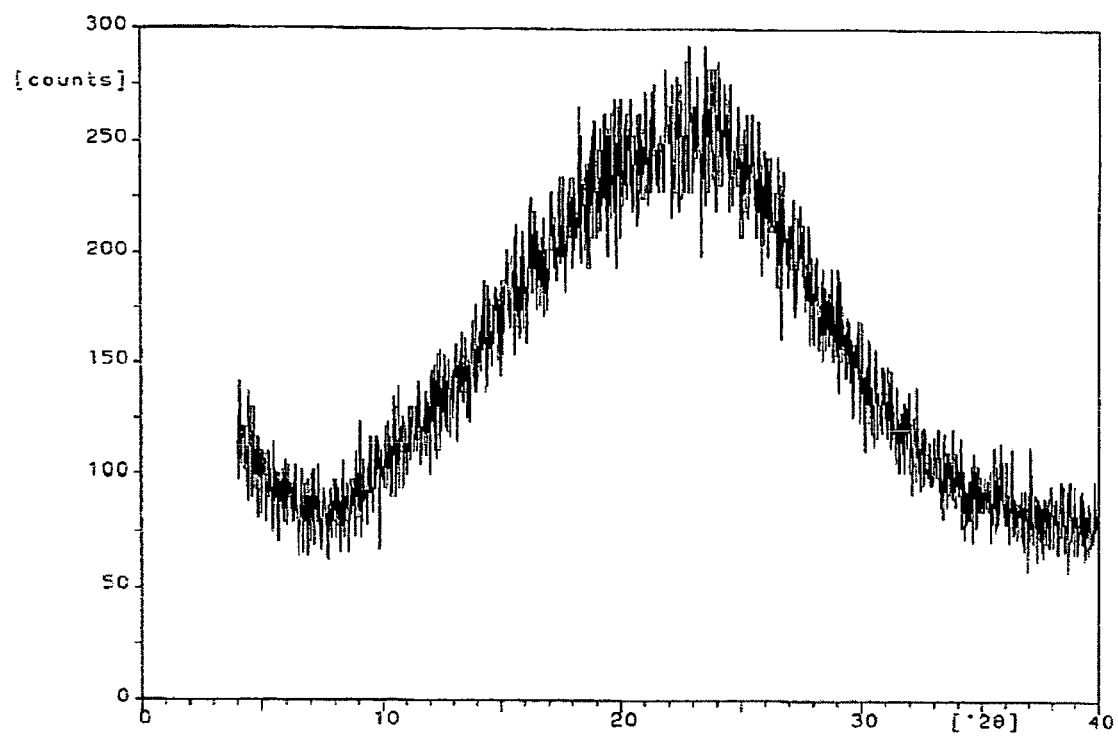

PREPARATION OF ACID ADDITION SALTS OF ZIPRASIDONE AND INTERMEDIATES THEREOF BY SOLID PHASE-GAS PHASE REACTIONS

FIELD OF INVENTION

The present invention relates to a new, useful and advantageous technique for the preparation of acid addition salts of ziprasidone by a gas phase/solid phase reaction.

BACKGROUND OF THE INVENTION

Ziprasidone hydrochloride (5-[2-[4-(1,2-benzisothiazol-3-yl)-1-piperazinyl]ethyl]-6-chloro-1,3-dihydro-2H-indol-2-one hydrochloride), I is a potent neuroleptic agent useful in the treatment of psychotic disorders, schizophrenia, and anxiety diseases. It is currently marketed under the proprietary name of Geodon.

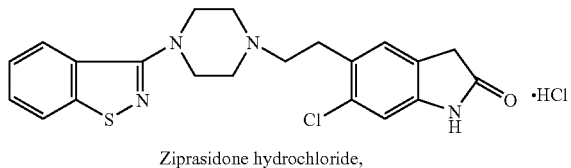

Ziprasidone hydrochloride,

Ziprasidone hydrochloride is known to exist in various crystalline forms; namely, the monohydrate, hemihydrate and anhydrate form as disclosed in U.S. Pat. Nos. 4,831,031 and 5,312,925. As well, Canadian patent application 2,471,219 teaches an improved process for the preparation of ziprasidone hydrochloride anhydrate and other novel forms of ziprasidone hydrochloride monohydrate are described in WO 2004/089948 A1.

A considerable amount of effort has been devoted to improving the physical properties of ziprasidone hydrochloride, for instance in terms of the particle size, purity and water solubility of the finished product. Purported solutions include:

1) the use of ziprasidone hydrochloride having a mean particle size of less than 85 µm (U.S. Pat. No. 6,150,366);

2) the use of ziprasidone hydrochloride having a particle size greater than about 85 µm and less than about 300 µm (US 2005/049295 A1);

3) the use of water soluble clathrates of ziprasidone and its salts (WO 2004/054621 A1);

4) alternate salt forms such as the mesylate salt (Canadian patent 2,252,898);

5) pro-drugs of ziprasidone (U.S. Pat. No. 5,935,960); and 6) amorphous and other forms of ziprasidone hydrochloride (WO 2004/050655 A1 where the product has a water content of about 0.5% to 7.5%, most preferably 4.0 to 4.5%, Canadian patent application 2,467,538, and US 2005/0043324 A1).

BRIEF DESCRIPTION OF THE DRAWINGS

FIG. 1 is a PXRD Diffractogram of Amorphous Ziprasidone Hydrochloride.

Although the process taught in Canadian patent application 2,467,538 furnished highly pure ziprasidone hydrochloride, it required the use of a solvent in the salt forming step which had to be removed from the finished product in order to be used as a pharmaceutical ingredient. Noteworthy is that the preparation of active pharmaceutical ingredients (API's) must meet high purity specifications, for instance in terms of residual solvent content and to this end, regulatory authorities have set out quality guidelines regarding the permissible amounts of residual solvent in active pharmaceutical ingredients (for example, International Conference on Harmonisation, guideline Q3C). The use of a solvent also added to the cost of the finished product and increased the volumes required in the final step.

It is therefore very desirable to have a novel process for preparing amorphous ziprasidone hydrochloride in high yields and purity which is more reliable, consistent and suitable for large scale manufacturing, thus helping to overcome the deficiencies of the prior art, for instance the need to remove residual solvent from the ziprasidone hydrochloride. In addition, a new process to alternate acid addition salts of ziprasidone having improved qualities such as the bulk density and particle size would be desirable.

SUMMARY AND DETAILED DESCRIPTION OF THE INVENTION

This invention pertains to the development of an original method for the preparation of acid addition salts including hydrochloride, hydrobromide and acetate salts of ziprasidone free base in the absence of solvent(s).

According to one aspect of the invention, there is provided a process for the preparation of an acid addition salt of ziprasidone comprising exposing the ziprasidone in solid form to at least one gaseous acid. This results in the formation of acid addition salts in high purity.

According to one aspect of the invention, there is thus provided a process for the manufacture of an acid addition salt of ziprasidone base, said process comprising exposing said ziprasidone base in solid form to an acid in gaseous form.

According to another aspect of the invention, there is provided a process for the manufacture of an acid addition salt of ziprasidone, said process comprising exposing said ziprasidone in solid form to an acid in gaseous form wherein the purity of the acid addition salt is substantially the same purity of the ziprasidone.

According to yet another aspect of the invention, there is provided a process of forming an acid addition salt of ziprasidone in a substantially solvent free environment which results in no additional residual solvent introduced during salt formation.

In one embodiment the acid used in gaseous form is a halo acid, even more preferably hydrogen chloride or hydrogen bromide.

In another embodiment the acid used in the gaseous form is an organic acid, preferably acetic acid.

In another embodiment, this invention is applicable to the preparation of acid addition salts of ziprasidone and intermediates thereof.

According to another aspect of the invention there is provided a process to manufacture an acid addition salt of ziprasidone in a substantially dry environment.

The gaseous acids may include haloacids such as hydrogen chloride (HCl) and hydrogen bromide (HBr) as well as organic acids, preferably weak organic acids, such as acetic acid.

The gaseous acid may comprise neat gas or a mixture of the gaseous acid and one or more inert gases. Examples of inert gases include such as nitrogen, argon and carbon dioxide.

Preferably any excess gaseous acid from the process is removed, collected and recycled.

A significant advantage of this method is that the desired salt form of the ziprasidone active pharmaceutical was produced having essentially the same purity as the starting free base. Furthermore, the salt forming step resulted in no additional residual solvent being introduced as was often the case using the prior art conditions wherein the salt formation is performed in solution by addition of an acid.

Other significant advantages of the instant invention is that it is readily scaleable for industrial production and permits a highly cost-effective and intrinsically safer process since it does not require the use of a solvent. The fact that a solvent is not required also permits better reactor utilization.

Also, this original method of salt formation is also useful to make novel and various polymorphs and forms having improved physical characteristics, for instance size, habit, and bulk density, relative to those obtained by prior art processes.

In a typical procedure for forming hydrogen halide addition salts, the free base is charged into a pressure-withstanding reactor. The reactor is purged with an inert gas, for example nitrogen, for a period of about 1 to 60 minute duration, preferably 2 to 10 minutes. The free base is adjusted to a suitable temperature, preferably −50° C. to 40° C. and the nitrogen is replaced with hydrogen halide gas, for instance hydrogen chloride or hydrogen bromide. The reactor is maintained at a pressure in the headspace equal to between about 0.1 to about 3 atm, preferably between about 1 to about 2 atm. The pressure is maintained by continuously supplying the hydrogen halide gas for about 1 to 24 hours duration, preferably 1 to 4 hours. It is preferable to gradually increase the pressure over the course of the reaction, for instance from about 0.1 to about 3 atm. The reaction pressure, temperature and time are chosen to obtain complete or near-complete conversion of the free base to the desired salt while minimizing or preventing the formation of impurities. The duration of the exposure of the free base to the hydrogen halide gas depends on various parameters such as batch size and the specific area of gas-solid contact. After the reaction, the hydrogen halide gas supply is discontinued, and the excess hydrogen halide gas is removed using nitrogen or by vacuum. It is important to note that this gas in recoverable and recyclable, thereby improving the efficiency of the process. Preferably, a stream of nitrogen is used for this purpose and the length of time is typically 5 to 120 minutes. The excess hydrogen halide gas is then removed from the product at a suitable temperature and at a suitable pressure, for instance between about 30 and about 100° C. and between about 0.001 and about 0.1 atm, to afford the hydrogen halide salt having the desired molar equivalents of hydrogen halide gas, typically 1.0 equivalents, and a purity higher than 98% per HPLC by area.

The acid gas mentioned can mean neat gas or a mixture of the acid gas and one or more inert gases.

In another embodiment, the free base is charged in an inclined baffled flask that can be rotated through its axis. The flask is rotated to create powder mixing. The advantage of mixing the free base is to reduce the reaction duration significantly by continuously exposing unreacted base to the gaseous acid and assist in dissipation of heat produced during the salt formation. On the other hand, the benefit of using inert gases is to help dissipate heat generated during the salt forming reaction and also to reduce the rate of reaction.

In another embodiment, the free base is charged in an inclined baffled flask that can be rotated through its axis. A neat inert gas, for instance nitrogen or argon is bubbled through a liquid organic acid, for instance acetic acid, and then the nitrogen gas is directed towards the mixed free base, thus efficiently taking acetic acid vapour to the free base. This method was useful to the preparation of organic acid addition salts such as acetate salts.

In another embodiment of the invention, the pressure of the acid gas can be gradually increased throughout the reaction in order to minimize impurity formation and decrease reaction time.

Once all the base has reacted, the obtained salt can be dried under a suitable vacuum at a controlled temperature to reduce the amount level of acid to the desired value.

Examples 1 to 4 describes the production of ziprasidone hydrochloride using this novel method, which has the characterizing powder X-Ray diffraction (PXRD) diffractogram shown in FIG. 1.

Example 5 describe the production of ziprasidone hydrobromide using this novel method.

Example 6 describes the production of ziprasidone acetate using this novel method.

While the products prepared by this method often have an amorphous form or a largely amorphous form, this does not limit this invention to a method only for the preparation of only amorphous salts.

EXAMPLES

Example 1

Preparation of Ziprasidone Hydrochloride (5-[2-[4-(1,2-benzisothiazol-3-yl)-1-piperazinyl]ethyl]-6-chloro-1,3-dihydro-2H-indol-2-one hydrochloride)

To a 1-L pressure-withstanding reactor equipped with a magnetic stirrer and hydrogen chloride inlet and purge valve was added 5-(2-(4-(1,2-benzisothiazol-3-yl)-1-piperazinyl)ethyl)-6-chloro-1,3-dihydro-2H-indol-2-one free base (10.0 g) and the powder was cooled to about 0-5° C. and at about 175 rpm the vessel was pressurized to a hydrogen chloride pressure of 20 psig. After about 5 minutes, the pressure had dropped to about 10 psig whereupon the pressure was increased to 20 psig. Over the next 10 minutes, the pressure had dropped to about 10 psig. The pressure was increased to about 20 psig and then was stirred for 18 hours at this pressure with continued agitation. The pressure was still at about 20 psig at which point the pressure was released and the vessel purged with nitrogen. The excess HCl was then removed from the powder in vacuo at 65-70° C. for about 5 h to afford ziprasidone hydrochloride (9.22 g) having the PXRD diffractogram FIG. 1. The purity by HPLC was 99.21%.

$^1$H NMR (300 MHz, DMSO-$d_6$) δ 3.15-3.25 (m, 2H), 3.30-3.48 (m, 4H), 3.50-3.80 (m, 6H), 4.05-4.20 (m, 2H), 6.91 (s, 1H), 7.31 (s, 1H), 7.50 (app.t, 1H), 7.63 (app. t, 1H), 8.14 (d, J=8.2 Hz, 1H), 8.19 (d, J=8.2 Hz, 1H), 10.59 (s, 1H), 11.42 (br. s, 1H).

Example 2

Preparation of Ziprasidone Hydrochloride (5-[2-[4-(1,2-benzisothiazol-3-yl)-1-piperazinyl]ethyl]-6-chloro-1,3-dihydro-2H-indol-2-one hydrochloride)

To a 1-L pressure reactor equipped a hydrogen chloride inlet and purge valve was added 5-(2-(4-(1,2-benzisothiazol-3-yl)-1-piperazinyl)ethyl)-6-chloro-1,3-dihydro-2H-indol-2-one free base (10.0 g) and the powder was cooled to about 0-5° C. The vessel was pressurized with hydrogen chloride to maintain a constant pressure of 20 psig over the powder for 6 hours, at which point the hydrogen chloride supply was discontinued. The pressure did not drop after this indicating complete reaction. The vessel was kept closed under the constant pressure of hydrogen chloride of 20 psig for an additional 4 hours at which point the hydrogen chloride was displaced with nitrogen. The excess HCl was then removed from the powder in vacuo at 60-65° C. to afford ziprasidone hydrochloride characterized by the Hnmr and X ray powder diffractogram as the material obtained in example 1. The purity of the ziprasidone hydrochloride was higher than 99.68%.

Example 3

Preparation of Ziprasidone Hydrochloride (5-[2-[4-(1,2-benzisothiazol-3-yl)-1-piperazinyl]ethyl]-6-chloro-1,3-dihydro-2H-indol-2-one hydrochloride)

To a 500 mL 3-necked-baffled flask was added 10 g of 5-(2-(4-(1,2-benzisothiazol-3-yl)-1-piperazinyl)ethyl)-6-chloro-1,3-dihydro-2H-indol-2-one (ziprasidone free base, 1). The flask was rotated with an electric motor to mix the powder and the flask was partially immersed in a temperature-regulated bath maintained at −2 Celsius to 0 Celsius. A stream a nitrogen was passed over the powder for 5 minutes and the nitrogen stream was stopped and replaced with a stream of hydrogen chloride. The hydrogen chloride flow was maintained for 2 hours whereupon the flow was stopped and replaced with a stream of nitrogen for 10 minutes. The excess HCl was then removed from the powder in vacuo at 60° C. for 12 hours. The product obtained was ziprasidone hydrochloride characterized by the Hnmr and X ray powder diffractogram as the material obtained in example. The purity of the ziprasidone hydrochloride obtained was 99.83% (HPLC).

Example 4

Preparation of Ziprasidone Hydrochloride (5-[2-[4-(1,2-benzisothiazol-3-yl)-1-piperazinyl]ethyl]-6-chloro-1,3-dihydro-2H-indol-2-one hydrochloride)

To a 1000 mL 3-necked baffled flask was added 100 g of 5-(2-(4-(1,2-benzisothiazol-3-yl)-1-piperazinyl)ethyl)-6-chloro-1,3-dihydro-2H-indol-2-one (ziprasidone free base, 1). The flask was rotated with an electric motor to mix the powder. The flask was partially immersed in a temperature-regulated bath maintained at −2 to 0° C. and a stream of nitrogen was passed over the powder for 5 minutes. The nitrogen flow was stopped and replaced with a stream of hydrogen chloride which was maintained for 5 hours whereupon the hydrogen chloride flow was stopped and replaced with a stream of nitrogen for 10 minutes. The excess HCl was then removed from the powder in vacuo at 60° C. for 12 hours. The product obtained was ziprasidone hydrochloride characterized by the Hnmr and X ray powder diffractogram as the material obtained in example. The purity of the ziprasidone hydrochloride obtained was higher than 98.5% (HPLC).

Example 5

Preparation of Ziprasidone Hydrobromide (5-[2-[4-(1,2-benzisothiazol-3-yl)-1-piperazinyl]ethyl]-6-chloro-1,3-dihydro-2H-indol-2-one hydrobromide)

To a 250 ml pressure-withstanding reactor equipped with a magnetic stirrer and hydrogen bromide inlet and purge valve was added 10.0 g of 5-(2-(4-(1,2-benzisothiazol-3-yl)-1-piperazinyl)ethyl)-6-chloro-1,3-dihydro-2H-indol-2-one (ziprasidone free base, 1). The reactor was purged with nitrogen for 3 minutes and then pressurized to a hydrogen bromide pressure of 15 psig and maintained at that level for 75 minutes. The sample was dried then in vacuo at 65-70° C. for about 3 hours to afford ziprasidone hydrobromide containing 1.6 equivalents of hydrogen bromide.

$^1$H NMR (300 MHz, DMSO-$d_6$) δ 3.10-3.25 (m, 2H), 3.30-3.55 (m, 8H), 3.70-3.85 (m, 2H), 4.05-4.20 (m, 2H), 6.90 (s, 1H), 7.31 (s, 1H), 7.48 (app. t, 1H), 7.61 (app. t, 1H), 8.12 (d, J=8.1 Hz, 1H), 8.18 (d, J=8.2 Hz, 1H), 10.20 (br. s, 1H), 10.55 (s, 1H).

Example 6

Preparation of Ziprasidone Acetate (5-[2-[4-(1,2-benzisothiazol-3-yl)-1-piperazinyl]ethyl]-6-chloro-1,3-dihydro-2H-indol-2-one acetate)

To a 1000 mL 3-necked baffled flask was added 10 g of 5-[2-[4-(1,2-benzisothiazol-3-yl)-1-piperazinyl]ethyl]-6-chloro-1,3-dihydro-2H-indol-2-one (Ziprasidone free base, 1). The flask was rotated with an electric motor to mix the powder and a stream of dry nitrogen was passed over the mixed powder for 2 minutes. The flow of nitrogen was then bubbled through pure acetic acid through a porous bubbler, and then passed over the mixed powder for 16 hours. Pure nitrogen was then passed over the powder for 20 min. The excess acetic acid was then removed from the powder in vacuo at 60° C. for 8 hr. The product obtained was 5-[2-[4-(1,2-benzisothiazol-3-yl)-1-piperazinyl]ethyl]-6-chloro-1,3-dihydro-2H-indol-2-one acetate containing approximately 2 equivalents of acetic acid.

$^1$H NMR (300 MHz, DMSO-$d_6$) 6) 1.91 (s, 3H), 2.50-2.60 (m, 2H), 2.65-2.75 (m, 4H), 2.80-2.90 (m, 2H), 3.45-3.55 (m, 6H), 6.81 (s, 1H), 7.24 (s, 1H), 7.43 (app.t, 1H), 7.56 (app. t, 1H), 8.06 (d, J=8.6 Hz, 2H), 10.42 (s, 1H), 11.97 (br. s, 1H).

While the following provides a detailed description of the preferred embodiments of the invention in the form of the examples given, it is to be understood that the descriptions in the examples are illustrative only of the principles of the invention and not limiting. Furthermore, as many changes can be made to the invention without departing from the scope of the invention, it is intended that all material contained in the examples be interpreted as illustrative of the invention and not in a limiting sense.

The embodiments of the invention in which an exclusive property or privilege is claimed are as follows:

1. A process for the preparation of an acid addition salt of ziprasidone base comprising reacting ziprasidone base in solid form with gaseous acid in a substantially dry environment thereby forming the acid addition salt of ziprasidone base, wherein the process is substantially solvent free.

2. The process of claim 1 wherein the process is solvent free.

3. The process of claim 1 further comprising agitation.

4. The process of claim 1 wherein the gaseous acid is mixed with one or more inert gases.

5. The process of claim 1 wherein reacting the ziprasidone base in sold form with gaseous acid is conducted at a temperature in the range of from about −50° C. to about 40° C.

6. The process of claim 1 wherein the acid is a hydrogen halide.

7. The process of claim 6 wherein the hydrogen halide is selected from the group consisting of hydrogen chloride and hydrogen bromide.

8. The process of claim 1 wherein the gaseous acid is an organic acid.

9. The process of claim 8 wherein the organic acid is acetic acid.

10. The process of claim 1 further comprising removal of excess acid.

11. The process of claim 10 wherein any excess gaseous acid from the process during the acid removal step is collected and recycled.

12. The process of claim 1 wherein the purity of the acid addition salt of ziprasidone base is substantially the same purity as the ziprasidone base in solid form.

13. The process of claim 1 wherein the process is conducted in a pressurized reactor.

14. The process of claim 13 wherein the reactor is maintained at a pressure of about 0.1 atm to about 3 atm.

15. The process of claim 14 wherein the pressure is about 1.0 atm to about 2.0 atm.

16. The process of claim 15 wherein the pressure is increased gradually over a period of time.

17. The process of claim 1 wherein the process is solvent free.

18. The process of claim 1 further comprising agitation.

19. The process of claim 1 wherein the gaseous acid is mixed with one or more inert gases.

20. The process of claim 1 wherein reacting the ziprasidone base in sold form with gaseous acid is conducted at a temperature in the range of from about −50° C. to about 40° C.

21. The process of claim 1 wherein the acid is a hydrogen halide.

22. The process of claim 21 wherein the hydrogen halide is selected from the group consisting of hydrogen chloride and hydrogen bromide.

23. The process of claim 1 wherein the gaseous acid is an organic acid.

24. The process of claim 23 wherein the organic acid is acetic acid.

25. The process of claim 1 further comprising removal of excess acid.

26. The process of claim 25 wherein any excess gaseous acid from the process during the acid removal step is collected and recycled.

27. The process of claim 1 wherein the purity of the acid addition salt of ziprasidone is substantially the same purity as the ziprasidone base in solid form.

28. The process of claim 1 wherein the process is conducted in a pressurized reactor.

29. The process of claim 28 wherein the reactor is maintained at a pressure of about 0.1 atm to about 3 atm.

30. The process of claim 29 wherein the pressure is about 1.0 atm to about 2.0 atm.

31. The process of claim 30 wherein the pressure is increased gradually over a period of time.

32. A process for the preparation of an acid addition salt of ziprasidone base comprising reacting ziprasidone base in solid form with gaseous acid, at a temperature in the range of from about −50° C. to about 40° C., in a substantially dry environment and agitating the ziprasidone base in solid form, thereby forming the acid addition salt of ziprasidone base, wherein the process is substantially solvent free.

33. The process of claim 32 wherein the process is solvent free.

34. The process of claim 32 wherein the acid is a hydrogen halide.

35. The process of claim 34 wherein the hydrogen halide is selected from the group consisting of hydrogen chloride and hydrogen bromide.

36. The process of claim 32 wherein the gaseous acid is an organic acid.

37. The process of claim 36 wherein the organic acid is acetic acid.

38. The process of claim 32 further comprising removal of excess acid.

39. The process of claim 38 wherein any excess gaseous acid from the process during the acid removal step is collected and recycled.

40. The process of claim 32 wherein the purity of the acid addition salt of ziprasidone base is substantially the same purity as the ziprasidone base in solid form.

41. The process of claim 32 wherein the process is conducted in a pressurized reactor.

42. The process of claim 41 wherein the reactor is maintained at a pressure of about 0.1 atm to about 3 atm.

43. The process of claim 42 wherein the pressure is about 1.0 atm to about 2.0 atm.

44. The process of claim 41 wherein the pressure is increased gradually over a period of time.

45. The process of claim 32 wherein the gaseous acid is mixed with one or more inert gases.

46. The process of claim 33 wherein the acid is a hydrogen halide.

47. The process of claim 46 wherein the hydrogen halide is selected from the group consisting of hydrogen chloride and hydrogen bromide.

48. The process of claim 33 wherein the gaseous acid is an organic acid.

49. The process of claim 48 wherein the organic acid is acetic acid.

50. The process of claim 33 wherein the purity of the acid addition salt of ziprasidone base is substantially the same purity as the ziprasidone base in solid form.

51. The process of claim 34 wherein the purity of the acid addition salt of ziprasidone base is substantially the same purity as the ziprasidone base in solid form.

52. The process of claim 35 wherein the purity of the acid addition salt of ziprasidone base is substantially the same purity as the ziprasidone base in solid form.

53. The process of claim 36 wherein the purity of the acid addition salt of ziprasidone base is substantially the same purity as the ziprasidone base in solid form.

54. The process of claim 37 wherein the purity of the acid addition salt of ziprasidone base is substantially the same purity as the ziprasidone base in solid form.

55. The process of claim 38 wherein the purity of the acid addition salt of ziprasidone base is substantially the same purity as the ziprasidone base in solid form.

56. The process of claim 46 wherein the purity of the acid addition salt of ziprasidone base is substantially the same purity as the ziprasidone base in solid form.

57. The process of claim 47 wherein the purity of the acid addition salt of ziprasidone base is substantially the same purity as the ziprasidone base in solid form.

58. The process of claim 48 wherein the purity of the acid addition salt of ziprasidone base is substantially the same purity as the ziprasidone base in solid form.

59. The process of claim 49 wherein the purity of the acid addition salt of ziprasidone base is substantially the same purity as the ziprasidone base in solid form.

60. The process of claim 33 wherein the process is conducted in a pressurized reactor at a pressure of about 1.0 atm to about 2.0 atm.

61. The process of claim 34 wherein the process is conducted in a pressurized reactor at a pressure of about 1.0 atm to about 2.0 atm.

62. The process of claim 35 wherein the process is conducted in a pressurized reactor at a pressure of about 1.0 atm to about 2.0 atm.

63. The process of claim 36 wherein the process is conducted in a pressurized reactor at a pressure of about 1.0 atm to about 2.0 atm.

64. The process of claim 37 wherein the process is conducted in a pressurized reactor at a pressure of about 1.0 atm to about 2.0 atm.

65. The process of claim 38 wherein the process is conducted in a pressurized reactor at a pressure of about 1.0 atm to about 2.0 atm.

66. The process of claim 46 wherein the process is conducted in a pressurized reactor at a pressure of about 1.0 atm to about 2.0 atm.

67. The process of claim 47 wherein the process is conducted in a pressurized reactor at a pressure of about 1.0 atm to about 2.0 atm.

68. The process of claim 48 wherein the process is conducted in a pressurized reactor at a pressure of about 1.0 atm to about 2.0 atm.

69. The process of claim 49 wherein the process is conducted in a pressurized reactor at a pressure of about 1.0 atm to about 2.0 atm.

70. The process of claim 50 wherein the process is conducted in a pressurized reactor at a pressure of about 1.0 atm to about 2.0 atm.

71. The process of claim 51 wherein the process is conducted in a pressurized reactor at a pressure of about 1.0 atm to about 2.0 atm.

72. The process of claim 52 wherein the process is conducted in a pressurized reactor at a pressure of about 1.0 atm to about 2.0 atm.

73. The process of claim 53 wherein the process is conducted in a pressurized reactor at a pressure of about 1.0 atm to about 2.0 atm.

74. The process of claim 54 wherein the process is conducted in a pressurized reactor at a pressure of about 1.0 atm to about 2.0 atm.

75. The process of claim 55 wherein the process is conducted in a pressurized reactor at a pressure of about 1.0 atm to about 2.0 atm.

76. The process of claim 56 wherein the process is conducted in a pressurized reactor at a pressure of about 1.0 atm to about 2.0 atm.

77. The process of claim 57 wherein the process is conducted in a pressurized reactor at a pressure of about 1.0 atm to about 2.0 atm.

78. The process of claim 58 wherein the process is conducted in a pressurized reactor at a pressure of about 1.0 atm to about 2.0 atm.

79. The process of claim 59 wherein the process is conducted in a pressurized reactor at a pressure of about 1.0 atm to about 2.0 atm.

* * * * *